US011293013B2

(12) United States Patent
Li

(10) Patent No.: US 11,293,013 B2
(45) Date of Patent: Apr. 5, 2022

(54) BIOMIMETIC AFFINITY PURIFICATION MATERIAL AND ITS APPLICATION IN CHITOSANASES PURIFICATION

(71) Applicant: QINGDAO UNIVERSITY, Qingdao (CN)

(72) Inventor: Shangyong Li, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 0 days.

(21) Appl. No.: 16/878,591

(22) Filed: May 19, 2020

(65) Prior Publication Data

US 2020/0277589 A1    Sep. 3, 2020

Related U.S. Application Data

(63) Continuation of application No. PCT/CN2019/111672, filed on Oct. 17, 2019.

(30) Foreign Application Priority Data

Nov. 9, 2018   (CN) .......................... 201811329059.X

(51) Int. Cl.
| | | |
|---|---|---|
| *C12N 9/24* | (2006.01) | |
| *C08B 37/00* | (2006.01) | |
| *B01D 15/38* | (2006.01) | |
| *B01J 20/32* | (2006.01) | |
| *B01J 20/289* | (2006.01) | |
| *B01J 20/26* | (2006.01) | |
| *B01D 15/22* | (2006.01) | |

(52) U.S. Cl.
CPC ........... *C12N 9/2402* (2013.01); *B01D 15/22* (2013.01); *B01D 15/3804* (2013.01); *B01J 20/267* (2013.01); *B01J 20/289* (2013.01); *B01J 20/3212* (2013.01); *B01J 20/3251* (2013.01); *B01J 20/3255* (2013.01); *B01J 20/3274* (2013.01); *C08B 37/0039* (2013.01); *C12Y 302/01132* (2013.01)

(58) Field of Classification Search
CPC ...... B01J 20/267; B01J 20/262; B01J 20/289; B01J 20/3212; B01J 20/3274; B01J 20/3255; B01J 20/3251; B01D 15/22; B01D 15/3804

See application file for complete search history.

(56) References Cited

U.S. PATENT DOCUMENTS

| | | | | | |
|---|---|---|---|---|---|
| 4,319,975 | A | * | 3/1982 | Cook | .................. C08B 37/0039 204/469 |
| 6,262,255 | B1 | * | 7/2001 | Mares-Guia | ........... A61K 9/009 424/443 |
| 2004/0175788 | A1 | * | 9/2004 | Galaev | ................. B01D 15/265 435/69.1 |
| 2005/0222279 | A1 | * | 10/2005 | Larsson | ................... B01J 20/26 521/50 |

FOREIGN PATENT DOCUMENTS

| | | |
|---|---|---|
| CN | 101078008 A | 11/2007 |
| CN | 108144586 A | 6/2018 |
| CN | 110038524 A | 7/2019 |

OTHER PUBLICATIONS

Liaqat et al. Chitooligosaccharides and their biological activities: A comprehensive review. Carbohydrate Polymers 184 (2018) 243-259. (Year: 2018).*
Li et al. Design and Synthesis of a Chitodisaccharide-Based Affinity Resin for Chitosanases Purification. Mar. Drugs 2019, 17, 68, 13 pg. (Year: 2019).*
Li et al. Structure-Based Design and Synthesis of a New Phenylboronic-Modified Affinity Medium for Metalloprotease Purification. Mar. Drugs 2017, 15, 5, 13 pg. (Year: 2017).*
Internation Search Report of PCT/CN2019/111672, dated Jan. 16, 2020.
Design and Synthesis of a Chitodisaccharide-Based Affinity Resin for Chitosanases Purification by Shangyong Li ,Linna Wang Xuehong Chen ,Mi Sun andYantao Han Mar. Drugs 2019,17(1), 68; https://doi.org/10.3390/md17010068—Jan. 21, 2019.
Office action of CN201811329059.X From State IPO of China, dated May 27, 2019.
Notice of Grant Patent Right for Invention From State IPO of China, dated Oct. 10, 2019.

* cited by examiner

*Primary Examiner* — Ryan B Huang
(74) *Attorney, Agent, or Firm* — W&KIP

(57) ABSTRACT

The invention relates to a novel biomimetic affinity purification material and its application in the purification of chitosanase, which belongs to the field of industrial biotechnology. The affinity ligand for the biomimetic affinity material is chitodisaccharides, the connecting arm is cyanuric chloride, and the base medium is epoxy-activated Sepharose™ 6B. The desorption constant (Kd) and the theoretical maximum adsorption capacity (Qmax) of the biomimetic affinity material are 24.2 μg/mL and 24.1 mg/g, respectively. Using the above biomimetic affinity material, a chitosanase biomimetic affinity purification method is established, which can produce high-purity chitosanase with high efficiency and low cost, and has good industrial application potential.

2 Claims, 4 Drawing Sheets

BIOMIMETIC AFFINITY PURIFICATION MATERIAL AND ITS APPLICATION IN CHITOSANASES PURIFICATION

CROSS-REFERENCE TO RELATED APPLICATIONS

This application is a continuation of International Patent Application No. PCT/CN2019/111672 with a filing date of Oct. 17, 2019, designating the United States, and claims priority to Chinese Patent Application No. 201811329059.X with a filing date of Nov. 9, 2018. The content of the aforementioned applications, including any intervening amendments thereto, are incorporated herein by reference.

TECHNICAL FIELD

The invention relates to a novel biomimetic affinity purification material and its application in the purification of chitosanase, which belongs to the field of industrial biotechnology.

BACKGROUND TECHNOLOGY

Chitosan is a derivative of chitin partially or completely deacetylated, which is mainly formed by D-glucosamine through the linkage of β-1,4-glycoside bonds. It is the only polysaccharide with positive charge in nature and is known as the sixth element of life. Chitosan oligosaccharide is a kind of functional oligosaccharide, which has the functions of antibacterial, anti-tumor, lowering blood lipid, lowering blood glucose, regulating the body's immunity, and promoting the increase of crop production. It is one of the hotspots of functional oligosaccharide research and development in recent years.

Chitosanase is a kind of glycoside hydrolase which catalyzes the β-1,4 glycoside bond breaking between glucosamine and specifically degrades chitosan. Traditional chitosanase purification requires multiple steps: ultrafiltration, ammonium sulfate precipitation, desalting, Q column ion exchange chromatography, Sephacryl™-200 gel column chromatography, etc. The entire purification process takes a long time, has a high cost, and has a low recovery rate. Compared with the traditional column chromatography method, the biomimetic affinity purification method has the advantages of strong specificity, simple operation and easy amplification. At present, some recombinantly expressed chitosanases have histidine tags, which can be purified by metal chelation chromatography, which can obtain higher purification efficiency. However, due to the particularity of metal chelating ligand, a large amount of toxic imidazole is needed in the process of metal chelating chromatography, which will affect the biological activity of purified chitosan enzyme, and the treatment of imidazole with desalting column will increase the additional steps and cost. Therefore, it is necessary to develop more specific biomimetic affinity materials to establish a biomimetic affinity purification method suitable for chitosanase.

Invention Content

In view of the deficiencies of the prior art, the present invention provides a novel biomimetic affinity material that uses chitodisaccharides as a biomimetic affinity ligand, the connecting arm is cyanuric chloride, and the basic medium is epoxy-activated Sepharose™ 6B. A bionic affinity purification method of chitosanase was established by using this material. The chitosanase biomimetic affinity method of the present invention has a simple purification method, low cost, and high purity, which is suitable for large-scale purification of chitosanase.

On the other hand, the present invention provides a synthesis method of a novel chitosanase biomimetic affinity material. Including the following 4 steps: 1) epichlorohydrin activated Sepharose™ 6B; 2) amination of Sepharose™ 6B; 3) connect the cyanuric chloride connecting arm; 4) chelate chitodisaccharides biomimetic affinity ligand.

On the other hand, the present invention also provides the application of the biomimetic affinity material in the biomimetic affinity purification of chitosanase.

On the other hand, the present invention also provides a method for measuring the desorption constant and maximum adsorption capacity of the biomimetic affinity material for chitosanase.

On the other hand, the present invention also provides a biomimetic affinity purification method of chitosanase, and the selected biomimetic affinity material is the material of the present invention.

Optimal selection: in the purification conditions, the loading buffer is glycine-NaOH, the buffer pH is 8.0~10.0, and the optimal loading pH is 8.6;

Optimal selection: in the purification conditions, the elution buffer is acetic acid-sodium acetate, the buffer pH is 4.0 to 6.0, and the optimal elution pH is 4.0;

Optimal selection: in the purification conditions, the loading concentration is 25~150 mg/mL, and the optimal loading concentration is 50 mg/mL;

Optimal selection: In the purification conditions, the NaCl concentration in the elution buffer is 0.2~1 M, and the optimal NaCl concentration is 0.8 M.

On the other hand, the present invention also provides an affinity column, and the packing is the biomimetic affinity material according to the present invention.

Benefits:

1. The chitosanase biomimetic affinity material of the present invention is a novel biomimetic affinity material, and the biomimetic affinity ligand used is chitodisaccharides, which has the following advantages: on the one hand, the preparation method of chitodisaccharides is simple, and it is the minimum degradation product of chitosanase, which can be combined with the specificity of chitosan enzyme, and can not be further degraded, so it is a natural excellent ligand; on the other hand, chitodisaccharide is an alkaline oligosaccharide, it has two amino groups naturally, which can be firmly combined with the connecting arm, providing convenient conditions for large-scale preparation of biomimetic affinity materials.

2. The chitosanase biomimetic affinity material of the present invention uses a circular connecting arm, which has strong mechanical strength, and the ligand is not easy to fall off. Moreover, the material has a strong affinity to chitosanase, and the maximum adsorption capacity ($Q_{max}$) of each gram of biomimetic affinity material to chitosanase CsnM is 24.1 mg/g. It is also easy to elute, with a desorption constant ($K_d$) of 24.2 µg/mL.

3. The chitosanase biomimetic affinity purification method established by using the biomimetic affinity material of the present invention is simple, low-cost, and easy to scale up. The protein purity of chitosanase CsnM reached above 95%. It is suitable for large-scale purification of chitosanase.

ILLUSTRATIVE DRAWINGS

SPECIFIC IMPLEMENTATION MODALITIES

Example 1 Synthesis Process of Biomimetic Affinity Materials

The synthesis process of biomimetic affinity materials includes four steps: 1) activation of Sepharose™ 6B by epichlorohydrin, which makes the Sepharose™ 6B in an active state to connect other groups; 2) amination of Sepharose™ 6B, and amino is added to the activated Sepharose™ 6B; 3) connect the cyanohydryl chloride connection arm, and cross-link the cyanohydryl chloride connection arm with the linked amino group; 4) chelate the biomimetic affinity ligand of chitodisaccharides and couple the biomimetic affinity ligand of chitodisaccharides on the connecting arm. The specific steps are as follows:

1.1 Epichlorohydrin Activated Sepharose™ 6B

Figure 1:
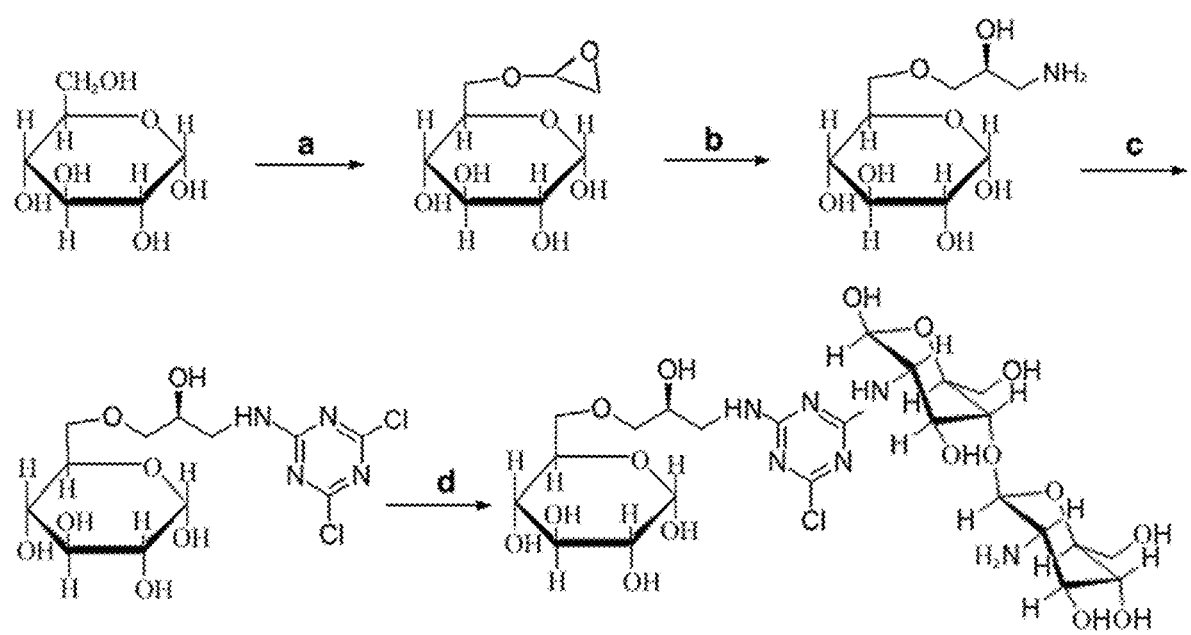
FIG. 1 is the synthesis process of the biomimetic affinity material.

The agarose gel (Sepharose 6B) was thoroughly washed by double steamed water at 1:10 (v/v) ratio, so that the pH of the effluent was equilibrated to 7. The washed Sepharose™ 6B was dried and dissolved at room temperature in 100 mL activation solution (1 M sodium hydroxide, 2.5 g dimethyl sulfoxide, and 10 mL epichlorohydrin), shaked at 40° C. in a shaker at 100 rpm for 2.5 h to obtain epichlorohydrin activated Sepharose™ 6B (FIG. 1a).

1.2 Amination of Sepharose 6B

The 35% saturated ammonia was added to the activated Sepharose 6B and incubated for 100 rpm at 30° C. in the shaking table for overnight. The activated Sepharose 6B was added to the amino group to obtain aminated activated Sepharose™ 6B (FIG. 1b).

1.3 Connect the Cyanuric Chloride Connecting Arm

Add 50% (v/v) acetone in equal volume to aminated activated Sepharose 6B, and slowly add cyanuric chloride solution (dissolved in 70 mL acetone) at a flow rate of 0.5 mL/min under ice bath stirring. The pH value of the solution was adjusted to 7 by 1 M NaOH solution, and then washed with 50% (v/v) acetone to remove the unbound amino group. The cyanuric chloride (connecting arm) was connected to the activated Sepharose™ 6B to obtain the biomimetic affinity ligand linking the cyanuric chloride connecting arm (FIG. 1C).

1.4 Chelating Chitodisaccharides Biomimetic Affinity Ligand

Dissolve the supersaturated biomimetic affinity material attached to the cyanuric chloride linking arm of step 1.3 in 2M sodium carbonate solution, and then slowly add twice the mass of chitodisaccharides to the sodium carbonate solution. After stirring at room temperature for 24 h, the Sepharose™ 6B was washed with double-distilled water and stored in 0.02% (W/V) sodium azide to obtain a biomimetic affinity material (FIG. 1d).

Example 2 Characterization of Biomimetic Affinity Materials

The biomimetic affinity material synthesized in example 1 is a macromolecular biomimetic affinity gel. In order to determine the ligand density of the biomimetic affinity material synthesized, the biomimetic affinity material synthesized in step 1.2 of example 1 was used ninhydrin method detects the density of amino groups in the biomimetic affinity material, thereby characterizing the ligand density of the synthetic biomimetic affinity material. The ninhydrin test showed that the density of the synthetic biomimetic affinity ligand reached 20.9 μmol/ml.

Figure 2:
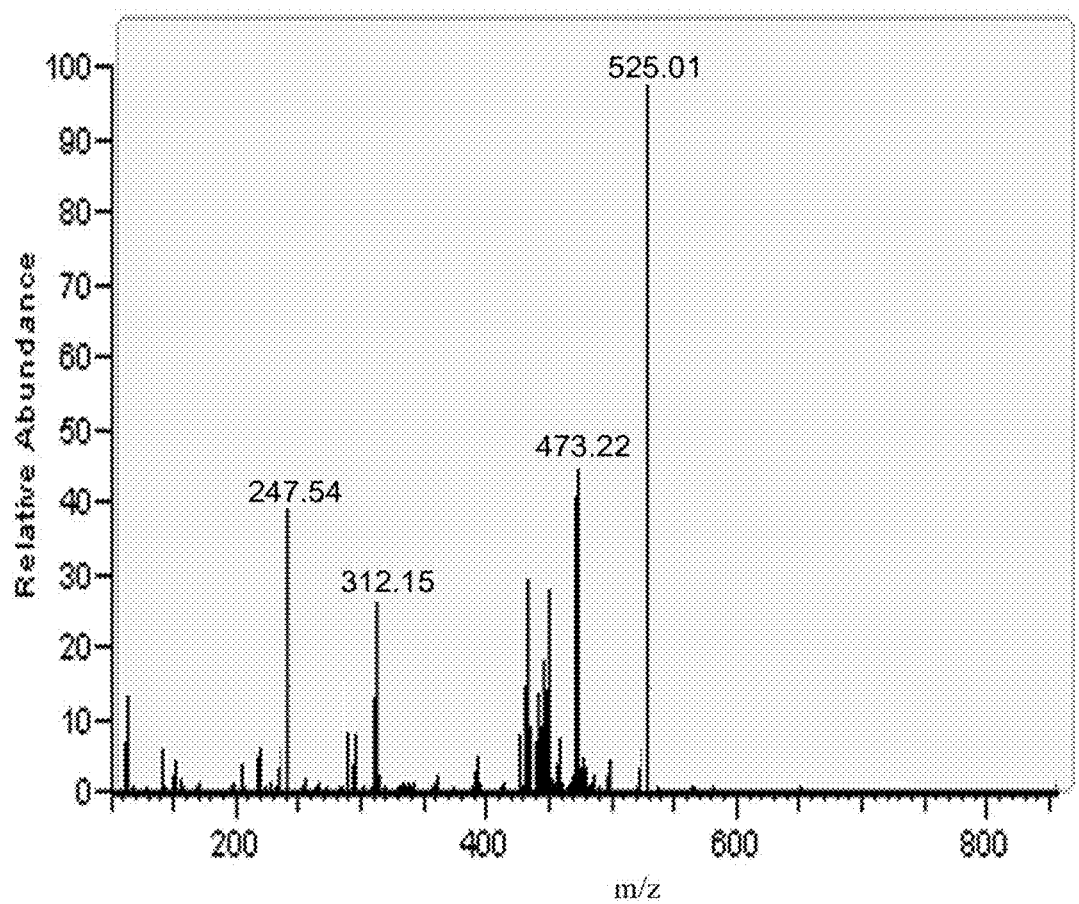
FIG. 2 is the mass spectrometry result of the biomimetic affinity ligand.

In order to determine the structure of the biomimetic affinity ligand in the synthetic biomimetic affinity material, the synthetic biomimetic affinity gel was added to 6 M concentrated hydrochloric acid in equal proportion (w/v). After 6 hours of action, it was centrifuged at 4000 rpm for 10 min. The clear solution was diluted 100 times with double-distilled water, and then an equal volume (v/v) of acetonitrile was added for mass spectrometry analysis. Theoretically, the biomimetic affinity ligand cleaved by 6M HCl is $C_{18}H_{31}ClN_6O_{12}$, and its relative molecular weight is 558.9. However, since the chloride ion is unstable in an acidic environment, it will be replaced by a hydroxyl group in 6 M HCl. Therefore, its molecular strain configuration is $C_{18}H_{32}N_6O_{12}$, and its relative molecular weight is 524.5. Mass spectrometry results (FIG. 2) show that the relative molecular weight of the biomimetic affinity ligand obtained by mass spectrometry is 525.01, which is consistent with the theoretical molecular weight of its positive ion first-order mass spectrometry.

Example 3 Desorption Constant and Maximum Adsorption Capacity of Biomimetic Affinity Materials Using the Scatchard equation method, the desorption constant ($K_d$) and maximum adsorption capacity ($Q_{max}$) of the biomimetic affinity material described in Example 1 were evaluated to determine the synthetic biomimetic affinity material for chitosanase CsnM adsorption and dissociation capacity. The used chitosanase CsnM was purchased from Qingdao Efit Biotechnology Co., Ltd.

Figure 3:
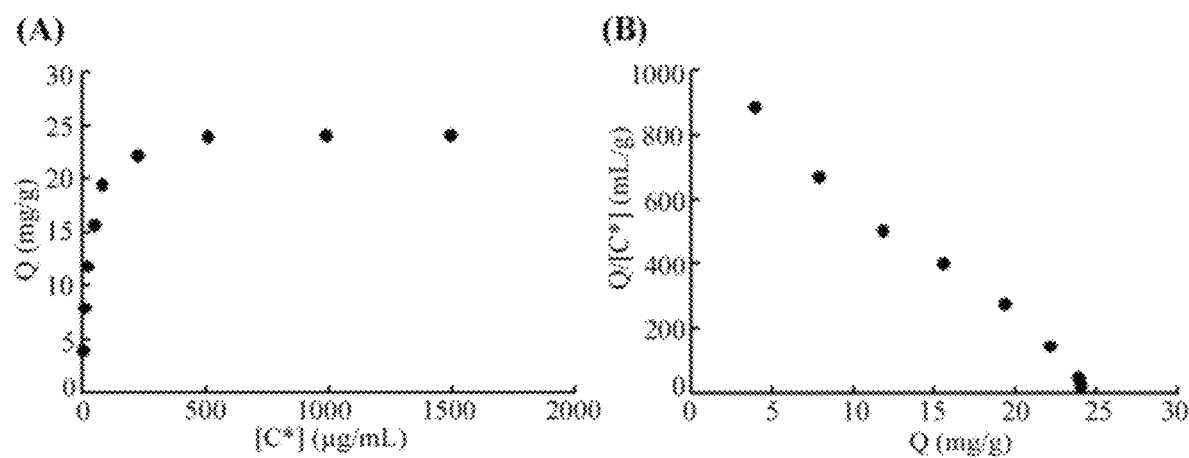
FIG. 3 is the desorption constant and maximum adsorption capacity of the biomimetic affinity material.

The specific measurement method is as follows: 1 mL of chitosanase CsnM of different concentrations (0.1-0.9 mg/mL, 20 mM Gly-NaOH, pH 8.6) is mixed with 0.5 g of the biomimetic affinity material described in Example 1. To incubate at 100 rpm with shaking at 4° C. for 2 h to reach adsorption equilibrium. The mixed solution was centrifuged at 1500 g for 5 min to detect the remaining protease activity and protein content in the supernatant. The measured data is calculated according to the Scatchard equation method:

$$Q = \frac{Q_{max}[C^*]}{K_d + [C^*]}$$

Where Q represents the amount of chitosanase adsorbed to the affinity resin (mg/g wet resin), $Q_{max}$ represents the theoretical maximum absorption of chitosanase to the affinity resin (mg/g wet resin), [C*] represents the protein concentration of chitosanase in the mixed solution (mg/mL), and $K_d$ represents the desorption constant. As shown in FIG. 3, the Scatchard equation method is used to calculate the figure. The desorption constant $K_d$ of the chitosanase CsnM described in Example 1 is 24.2 μg/ml; the maximum adsorption capacity $Q_{max}$ is 24.1 μg/g.

Example 4 Conditional Screening of the Biomimetic Affinity Purification Method of Chitosanase 30 mg of CsnM enzyme powder was diluted to 1 mL of the sample buffer (0.1 m tris-hcl, pH 8.0) and loaded with an affinity column of the biomimetic affinity material described in Example 1 (column length 25 mm×7 mm) after being filtered by 0.22 M of filter membrane to balance. The adsorption equilibrium buffer was used to balance the system until no protein peaks appeared. Then elution buffer was used to elute the column and collect the active components. The invention optimizes various elution and sample feeding conditions in the purification process.

4.1 Biomimetic Affinity Column Loading Condition Screening

Before loading, the biomimetic affinity material described in Example 1 was washed with 5-10 column volumes of double distilled water filtered with 0.22 μm, and then the column was equilibrated with 5-10 column volumes of loading buffer. The flow rate is 1 mL/min and the column pressure is protected (less than 0.3 mPa). According to the purification results, select the most suitable loading buffer type, buffer pH, and loading volume.

4.1.1 Optimal Loading Buffer

Five kinds of common basic buffers, which can reach pH 9.0, were selected to purify chitosanase by FPLC. They are sodium barbiturate hydrochloric acid, glycine sodium hydroxide, boric acid borax, disodium hydrogen phosphate potassium hydrogen phosphate and sodium carbonate sodium bicarbonate. Collect the elution peak sample and determine the purity, and compare the purification effect of five kinds of elution buffer. Through the analysis of the purification results, it can be seen that glycine sodium hydroxide buffer has the largest amount of protein purified, and the buffer has little damage to affinity column. Therefore, glycine sodium hydroxide was selected as the buffer.

4.1.2 Optimum Loading Buffer pH

Glycine-sodium hydroxide buffer solutions of different pH were prepared, and chitosanase was purified by FPLC. The specific enzyme activity of the elution peak samples was measured, and the influence of different pH loading buffers on the purification effect was analyzed. Through purification efficiency analysis, it was found that the pH of the glycine-sodium hydroxide buffer was 8.6, and the elution effect was the best. Therefore, the pH of the buffer was 8.6.

4.1.3 Optimal Loading Volume

Six kinds of enzyme solutions with different concentrations of 25 mg/mL, 50 mg/mL, 75 mg/mL, 100 mg/mL, 125 mg/mL, and 150 mg/mL were prepared, and the effects of different loading concentrations on the purification effect were investigated. It was found that the optimal loading concentration was 50 mg/mL and the loading volume was 1 mL.

4.2 Washing to Remove Impurities

According to the sample of chitosanase described in 4.1.3, load the sample to the biomimetic affinity column balanced in 4.1, the flow rate is 1 ml/min, wash 5-10 column volumes with washing buffer A, remove the impurities, the washing flow rate is 1.5 ml/min, the column pressure is not more than 0.3 MPa, and the washing buffer a is 100 mm glycine sodium hydroxide buffer containing 100 mm NaCl (pH 8.6).

4.3 Elution to Obtain Pure Chitosanase

After removing contaminants according to the method described in 4.2, eluted with wash buffer B and collected the activity peak, which was the pure enzyme of chitosanase, the elution flow rate was 1.5 ml/min, the column pressure does not exceed 0.3 mPa. Choosed the lowest can reach the five common acidic pH 4.0 buffer acetate, sodium acetate, sodium citrate, citric acid, disodium hydrogen phosphate and citric acid, acetic acid, citric acid, sodium hydroxide and hydrochloric acid, potassium acetate, using implementation Example 1 described in biomimetic affinity materials for separation and purification, chitosan enzyme CsnM collection elution peak and its measurement than the enzyme activity. Based on the elution results and cost, the elution buffer was determined to be acetic acid-sodium acetate buffer.

Preparing elution buffers of different pH, chitosan enzyme was purified by protein purification chromatograph (FPLC) under the condition that other conditions were unchanged. The enzyme specific activity of the elution peak sample was measured, the effect of elution buffer with different pH on the purification was analyzed, and the optimum elution buffer pH was determined. Three different pH conditions (3.0, 4.0, 5.0, 6.0) were prepared with acetic acid-sodium acetate buffer to perform chromatographic purification. The results showed that the lower the pH, the higher the amount of purified protein. However, considering that low pH would damage the enzyme activity, the elution pH was chosen to be 4.0.

Adding NaCl to the elution buffer can significantly improve the efficiency of eluting chitosanase. By optimizing the NaCl concentration, the optimal NaCl concentration was determined as 0.8 M. The washing buffer was determined to be 100 mM acetic acid-sodium acetate buffer (pH 4.0) containing 0.8 M NaCl, and the washing buffer B was 100 mMTris-HCl buffer (pH 8.0) containing 0.8 M NaCl.

4.4 Wash and Save the Column

Washed the column with washing buffer C to remove the protein firmly bound to the column, then rinsed 5-10 column volumes with 0.22 μm filtered double distilled water to remove various salt ions in the washing buffer, then used 20% store the column in ethanol. The washing buffer C was 100 mMTris-HCl buffer (pH 8.0) containing 2 M NaCl.

Example 5 Biomimetic Affinity Purification Method of Chitosanase CsnM

According to the optimal conditions of each influencing factor explored in Example 4, the chitosanase powder was filtered through a 0.22 μm filter membrane to an equilibrium affinity column loaded with the biomimetic affinity material described in Example 1. Washed 5-10 column volumes with adsorption equilibration buffer (glycine-sodium hydroxide pH 8.6) until the system equilibrates, no protein peaks appear, the flow rate was 1 mL/min, and the column pressure was set to protect (less than 0.3 mPa). The loading concentration was 50 mg/mL and the loading volume was 1 mL. After loading the sample, first washed the column with washing buffer A to remove impurities, and then washed the column with washing buffer B to obtain the protein of interest. Then washed the column with wash buffer C to remove strongly bound contaminants. The column was stored in 20% ethanol.

Example 6 Determination of Purity of Chitosanase

Figure 4:
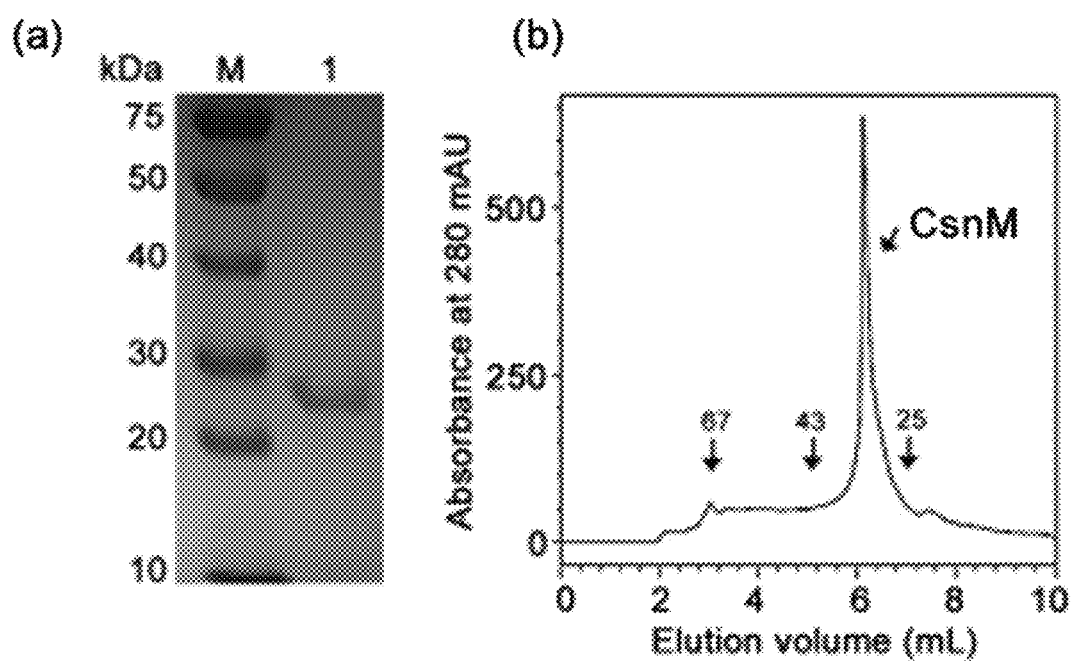
FIG. 4 is a purification assay of chitosanase purified by the biomimetic affinity method of the present invention: a is the purity of chitosanase CsnM by SDS-PAGE method; b is the purity of chitosanase CsnM by HPLC method.

The protein denaturing electrophoresis (SDS-PAGE) method was used to detect the chitosanase CsnM purified in Example 5 for SDS-PAGE purity analysis: the concentration of the separating gel was 10%, and the concentration of the concentrated gel was 5%. The purified sample was added to 2×Loading Buffer in a medium volume, boiled in 100° C. boiling water for 5 min, and subjected to SDS-PAGE electrophoresis analysis in a BioRad vertical electrophoresis tank. The voltage of the concentrated gel was 80 V, and the voltage in the separation gel was 120 V, and the electrophoresis time was controlled by the color of bromophenol blue. After electrophoresis was completed, it was stained with Coomassie Brilliant Blue R-350, decolorized with a decolorizing solution, and then photographed in an automatic gel imaging system and analyzed for purity. As shown in FIG. 4a, the protein purity of the chitosanase CsnM obtained by SDS-PAGE analysis was 96.7%.

The samples obtained by the purification method in Example 5 were subjected to purity analysis by high-performance liquid chromatography (HPLC). The TSK3000SW gel filtration column was used for detection at a wavelength of 280 nm. The mobile phase was 100 mM PBS, 100 mM Na2SO4, 0.05% NaN3, and the flow rate was 0.6 mL/min. As shown in FIG. 4b, by calculating the peak area of HPLC, the protein purity of the purified chitosanase CsnM was 95.9%.

I claim:

1. A biomimetic affinity material, comprising a biomimetic affinity ligand, a connecting arm, and a basic medium, wherein the biomimetic affinity ligand is chitodisaccharides, the connecting arm is cyanuric chloride, and the basic medium is epoxy-activated agarose gel.

2. A method for preparing the biomimetic affinity material according to claim 1, wherein the steps are as follows:
   1) activating an agarose gel with epichlorohydrin to form the epoxy-activated agarose gel;
   2) aminating the epoxy-activated agarose gel to form an aminated agarose gel;
   3) connecting the cyanuric chloride connecting arm to the aminated agarose gel; and
   4) chelating the chitodisaccharides biomimetic affinity ligand to the cyanuric chloride connecting arm.

* * * * *